United States Patent
Morris

(10) Patent No.: US 6,300,539 B1
(45) Date of Patent: Oct. 9, 2001

(54) MODEL FOR CHRONIC CEREBRAL INFLAMMATION BY INTRACEREBRAL INJECTION OF DOUBLE STRANDED RNA

(75) Inventor: Christopher Miles Morris, Northumberland (GB)

(73) Assignee: Medical Research Council, London (GB)

(*) Notice: Subject to any disclaimer, the term of this patent is extended or adjusted under 35 U.S.C. 154(b) by 0 days.

(21) Appl. No.: 09/381,607

(22) PCT Filed: Mar. 26, 1998

(86) PCT No.: PCT/GB98/00933

§ 371 Date: Dec. 30, 1999

§ 102(e) Date: Dec. 30, 1999

(87) PCT Pub. No.: WO98/43476

PCT Pub. Date: Oct. 8, 1998

(30) Foreign Application Priority Data

Mar. 27, 1997 (GB) .................................. 9706463

(51) Int. Cl.[7] .......................... A01K 67/00; A01N 43/04; A01N 31/70
(52) U.S. Cl. ................... 800/9; 514/44; 514/45; 514/49; 800/14; 800/21
(58) Field of Search .............. 514/44; 536/23.1, 536/24.5; 435/455, 1.1; 800/14, 21

(56) References Cited

FOREIGN PATENT DOCUMENTS

| 8219 | 9/1970 | (FR) . |
|---|---|---|
| WO 95/20666 | 8/1995 | (WO) . |
| WO 95/22616 | 8/1995 | (WO) . |

OTHER PUBLICATIONS

Allen et al. Infection and Immunity 6(5):819–823, Nov. 1972.*
Kleischmidt et al. Nature 220(163):167–168, Oct. 1968.*
Pachner et al. Neurology 45(1):165–172, Jan. 1995.*
Allen, L.B. and Cochran, K.W., "Acceleration of scrapie in mice by target organ treatment with interferon inducers" Third Conf. on Annals of the New York Academy of Sciences: Antiviral Substances, vol. 284:676–681 (1977).
Allen, L.B. and Cochran, K.W., "Target–organ treatment of neurotropic virus disease with interferon inducers". Infection and Immunity vol. 6(5):819–923 (1972).
Smalley, R.V. and Stringfellow, D.A., "Interferon inducers: preclinical and clinical studies" in Interferon vol. 4 :in vivo and clinical studies, ed. Finter, N.B. & Oldham, R.K. (Elsevier Science, Amsterdam) (1985).

* cited by examiner

Primary Examiner—Jill D. Martin
Assistant Examiner—Joseph T. Woitach
(74) Attorney, Agent, or Firm—Mathews, Collins, Shepherd & Gould, P.A.

(57) ABSTRACT

A method of producing a non-human mammalian model of chronic cerebral inflammation is disclosed. The method comprises introducing into the mammal's brain a polynucleotide that does not encode amyloid precursor protein (APP). Applicants have discovered that APP expression is not necessary to mimic the symptoms of human neurodegenerative diseases. The mammalian models mimic in an in vivo system some of the physical manifestations of diseases of the central nervous system, such as Alzheimer's disease, Parkinson's disease, multiple sclerosis, and encephalopathies. The models are useful in screening putative prophylactic and therapeutic compositions for addressing symptoms of chronic cerebral inflammation.

19 Claims, No Drawings

MODEL FOR CHRONIC CEREBRAL INFLAMMATION BY INTRACEREBRAL INJECTION OF DOUBLE STRANDED RNA

This application is a 371 filing of PCT/GB98/00933, filed Mar. 26, 1998.

FIELD OF THE INVENTION

The present invention relates to an animal model for use in the study of human diseases, conditions and disorders, especially neurodegenerative diseases, that are characterized by the damage or dysfunction of the central nervous system. The present invention also relates to compositions used in the generation of said animal model.

BACKGROUND OF THE INVENTION

Several chronic and acute degenerative disorders of the central nervous system (CNS) show as part of their pathology the presence of reactive brain macrophages or microglial cells. These microglial cells are associated with the pathological lesions of the disease in question. It has been suggested that the presence of these cells is either the cause of these diseases, or that microglia play a major role in their progression and outcome. The presence of microglial cells in these disease states is suggested to indicate an inflammatory or immune response within the brain.

Many human neurodegenerative disorders are characterized by such physical and biochemical pathology. Of these, Alzheimer's disease (AD) is the most common, characterized by a progressively worsening and debilitating dementia.

Alzheimer's disease affects millions of individuals of all races and ethnic backgrounds. The number of sufferers is expected to expand markedly as the proportion of the aged in the population increases (Plum, 1979). While some intellectual dysfunction is a natural result of the aging process, the dementia caused by AlzheimerIs disease is by no means normal. After onset of the disease, life expectancy ranges from only five up to twenty years.

There is presently no treatment that will arrest the progression of Alzheimer's disease. Clinical trials have been instigated involving the use of agents from such diverse pharmaceutical classes such as cerebral vasodilators, CNS stimulants, neuroleptics, nootropics, receptor stimulants, neuropeptides, aminergic enhancers and cholinergic enhancers. The results of these trials have all been disappointing to date.

The brains of individuals suffering from AD are characterized by prominent neuropathologic lesions, such as neurofibrillary tangles (NFTS), neuropil threads (NT) and amyloid-rich senile plaques (SP). These lesions are associated with massive loss of populations of CNS neurones and their development invariably accompanies the clinical dementia associated with AD. Thus, the reproduction of such lesions in an animal would provide a valuable model for the study of the development and progression of AD. Equally, the model would also provide for the screening of putative prophylactic and therapeutic compositions. Szczepanik et al., 1996 have reported an acute inflammatory response and the formation of necrotic lesions upon intrahippocampal infusion of lipopolysaccharides. Such a system is, however, unsuitable as a model for the chronic inflammatory response observed in AD.

At present, the only source f or study of the physical manifestations of AD in the CNS is from cadaver specimens. Although useful from an anatomical perspective, such material can provide little indication of the early progression of AD and is of no use in the design of therapies to counter the development of the lesions. Thus, prospective models of NFT and SP development that may or may not form the basis for the targeting of prophylactic pharmaceuticals are impossible to validate or disprove.

There is thus a great need for animal models of CNS diseases, conditions and disorders. There is also a need for animals that develop or mimic similar pathology and symptoms to those manifested in human sufferers and for a method that identifies compounds useful in the generation of such a model.

Such a model would be invaluable in the evaluation, of prospective treatments for CNS disease, including the assessment of therapeutic or prophylactic pharmaceutical preparations, or alternative non-invasive strategies. Suitable diseases that could be studied by such a technique include any whose symptoms are manifested through chronic cerebral inflammation. Examples include Alzheimer's type senile dementia, Lewy Body dementia, Parkinson's disease, Multiple sclerosis, transmissible spongiform encephalopathies, motor neuron disease and viral encephalopathies.

SUMMARY OF THE INVENTION

The present invention relates to a method of producing an animal model of chronic cerebral inflammation, comprising the step of introducing into said animal's brain a polynucleotide.

By chronic cerebral inflammation is meant the time-extended inflammation for periods of more than four days duration which results in the presence of microglial cells, invading leucocytes, and resident astrocytes in a state of hyperactivity not present in the normal brain.

By microglial cell is meant a cell of mesenchymal origin found within the CNS and peripheral nervous system (PNS) and derived either from resident progenitor cells of the CNS or from cells of the monocyte/macrophage lineage entering the brain from the circulation. These cells have a characteristic morphology and can be demonstrated by various staining methods. They represent the macrophage component of the brain (Barron, 1995).

The method of introduction into the brain may comprise any physical method of introduction of material into the brain parenchyma, an anatomical region of the CNS or the cerebrospinal fluid. Such methods include injection by miniosmotic pump, by needle, syringe or similar mechanism, or introduction by microdialysis. Preferably the composition is introduced by means of a mini-osmotic pump.

The invention also relates to compositions useful in the generation of such a model. These compositions may be in liquid, gel or solid form and may comprise a polynucleotide or mixture of polynucleotides. Preferably the compound is in a liquid form.

The polynucleotide may comprise any polynucleotide capable of generating a chronic inflammatory response. Preferably, the polynucleotide is 50 to 10,000 base pairs in length, more preferably 100 to 10,000 base pairs in length. Such polynucleotides include double or single-stranded polynucleotides. The polynucleotide may comprise ribonucleic acid (RNA), deoxyribonucleic acid (DNA), a polynucleotide analogue or a mixture of two or more of these compounds. Polynucleotide analogues include polynucleotides comprising modified chemical groups. Modifications may be present in one or more of the saccharide, purine/pyrimidine base or phosphate linkage parts of the molecule.

Polynucleotide analogues also include hybrid polynucleotides such as hybrid RNA-DNA molecules and hybrid peptide-nucleic acid molecules. Additionally, the polynucleotide may be either natural, recombinant or synthetic in derivation. Preferably, the polynucleotide is exogenous to the animal; more preferably exogenous to the animal species. Where a natural polynucleotide preparation is employed, the polynucleotide is preferably in substantially isolated form. Preferably the polynucleotide is substantially free of cellular proteins and other non-polynucleotide cellular material. Preferably the composition comprises double-stranded RNA. More preferably, the composition comprises double-stranded synthetic RNA.

Introduction into the animal brain of the polynucleotide is characterized by one or more of the following effects:

i) activation of microglia in the CNS, in particular in the hippocampus, cortex and thalamus;
ii) induction of Interleukin-1β;
iii) tissue becomes hyperaemic--;--
iv) deposition of ubiquitin;
v) deposition of amyloid precursor protein;
vi) deposition of β4 immunoreactive inclusions; and
vii) loss of neurons in the hippocampus and thalamus and other brain regions. As related above, the polynucleotide molecule itself produces one or more of the above effects. The polynucleotide used in the invention does not encode APP.

Activated microglial cells can be differentiated from inactive microglial cells by immunochemistry. Activated cells express the MHC class II antigen, upregulate the Complement protein 3 receptor and exhibit an increased ability to bind to lectin. Histological examination of these cells reveals their more bushy appearance and more densely absorbed, slightly retracted processes.

According to a further aspect of the present invention, there is provided an animal for use as a model of chronic cerebral inflammation and/or a neurodegenerative disease wherein the animal has had introduced into its brain a polynucleotide according to the present invention.

Any non-human animal may be used to generate models of cerebral inflammation as described herein. Preferably, the animal is a mammal. More preferably, due to their ease of handling, care and breeding, rodents may be used. The rodent of choice is the rat.

Preferably, the polynucleotide is introduced directly into the brain of the animal. However, where the polynucleotide is capable of crossing the blood-brain barrier, the polynucleotide may be administered systemically. In order to accurately mimic the manifestations of neuropathology exhibited in neurodegenerative disorders, the composition is preferably introduced into the anatomical region of the brain of the animal, or into the cerebrospinal fluid.

According to a further aspect of the present invention there is provided a method of testing the therapeutic and/or prophylactic properties of a chemical compound against a chronic cerebral inflammation and/or a neurodegenerative disease comprising administration of the chemical compound to an animal according to the present invention.

All documents mentioned in the text are incorporated by reference.

Various aspects and embodiments of the present invention will now be described by way of example. It will be appreciated that modification of detail may be made without departing from the scope of the invention.

EXAMPLES

Implantation of Mini-osmotic Pumps for I.C.V. Infusion of Inflammatory Agents

1. Preparation of Inflammatory Agents

A 2 mg/ml stock solution of Statolon (a kind gift from Eli Lilly Corporation, Indianapolis, USA) and a 10 mg/ml stock solution of polyinosinic-polycytidilic acid (PIPC) (available as a sterile gamma irradiated sodium salt from Sigma, Dorset, U.K. or sterilized by passing through a 0.22 μm filter) dissolved in Tris Borate EDTA buffer (TBE; 89 mM Tris base, 89 mM Boric acid, 2 mM EDTA, pH 8.0) were prepared.

TBE was made with, autoclaved water to minimize RNAase activity prior to infusion. The TBE was also filtered through a 0.22μ filter before use to ensure complete sterility and the absence of particulate matter which might block the pump. The stock solutions were stored at −70° C. until required.

For use, aliquots of Statolon or PIPC were defrosted and the solutions were heated to 60° C. for approximately 30 minutes to ensure that the dsRNA was fully dissolved. Any remaining particulate matter was removed by centrifugation at 13,000 rpm for 5 minutes (Koolspin μP, Burkard). Solutions were then diluted to their working concentrations in sterile, filtered TBE. Sterile conditions were maintained throughout.

2. Preparation of Mini-osmotic Pumps for Brain Infusion

Gloves were worn throughout all parts of the procedure to prevent contamination of the pumps with micro-organisms or with skin oils that affect their osmotic activity. The catheter tubing provided with the brain infusion kit (Brain Infusion Kit 3–5 mm, list No. 4760-0, Alza Corporation, Palo Alto, Calif. 94303, USA comprising a cannula for insertion into the brain, a set of plastic spacers to allow for varying the depth of the cannula, and a piece of plastic tubing to connect the cannula to the pump) was cut to a length suitable to cover the distance between the nuchal position of the pump and the brain infusion site and to allow free movement of the rat's head. The tubing was attached to the brain infusion cannula and to the flow moderator of the pump. Using a spare piece of catheter tubing attached to the free end of the flow moderator, a sterile syringe and the blunt-ended filling needle (provided with the brain infusion kit), the flow moderator, the catheter and cannula were all filled with the solution containing the inflammatory agent. Great care was taken not to introduce any bubbles. The flow moderator was inserted into the pump and the complete assembly was pre-incubated overnight in sterile universal tubes containing sterile saline at 37° C. Pre-incubation allows immediate delivery of the inflammatory agent to the brain as soon as the pump is implanted and provides a level of flow which minimizes the risk of clotting within the cannula or occlusion with tissue during implantation.

3. Surgical Implantation of Mini-osmotic Pumps

Rats were anaesthetized with an intraperitoneal injection of 0.4 ml/100 g of Equithesin [81 ml Nembutal (Abbott), 198 ml of Propane-1, 2-diol (Fisons), 21.25 g Chloral Hydrate (Sigma), 10.63 g Magnesium sulphate dissolved in 50 ml absolute alcohol and made up to 500 ml with distilled water]. (Alternatively any recommended anaesthetic as prescribed in a current small animal surgery textbook such as, 1:1 Hypnorm (Janssen): Hypnovel (Roche) at 3.3 ml/kg i.p. may be used). The head of the rat was shaved and swabbed clean with 70% alcohol. Rats were placed in a stereotaxic frame (David Kopf Instruments, Jujunga, Calif., USA) with incisor bar at horizontal zero. A full thickness incision was made in the scalp and the skull scraped clean of periosteal connective tissue. A hole was drilled through the full thickness of the skull at the following co-ordinates according to the atlas of Paxinos and Watson (Paxinos and Watson, 1986); Anterior-Posterior 0.8 mm posterior to bregma, Lateral 1.8 mm left of midline. This was to allow the implantation of the stainless steel L-shaped 25 gauge cannula of the brain infusion kit into the left lateral ventricle. Three further holes were drilled in a 3–4 mm radius of the cannula hole to allow placement of three anchor screws. A subcutaneous pocket was made by blunt dissection in the nuchal region in order to accommodate the pump. Once the pump was in position, the catheter was lead to the site for infusion and the electrode manipulator attachment of the stereotaxic frame was used to insert the cannula to a depth of 3.4 mm below the dura. This was achieved using one of the spacers provided with the kit. The cannula was secured in place by the application of dental cement covering the cannula and the anchor screws.

Once the cement was dry, the electrode manipulator arm was withdrawn and the placement tab removed. The scalp incision was closed with 3–4 metal sutures and the wound dusted with Aureomycin antibiotic powder (Cyanamid, UK). The rats were removed from the stereotaxic frame and allowed to recover.

Infusion of Inflammatory Agents 0.15 mg/ml Statolon or 0.2 mg/ml PIPC in TBE was pumped at the rate of 0.5μl/hour into the left lateral ventricle via an Alzet mini-osmotic pump (Charles River UK Ltd.), at the level of the fimbria-fornix, for a period of 14 days.

Rats were allowed to survive to 28 days from the start of the infusion. They were perfusion fixed; then the brains were removed and embedded in paraffin wax.

1. Lectin Histochemistry for Microglial Cells

Immunocytochemistry for the amyloid precursor protein (Hilbich et al., 1993) and MHC class II antigen (rat Ia) expression (expressed by activated microglial cells), and lectin histochemistry to identify microglial cells, was carried out on 6 μm microtome sections.

Lectin histochemistry was carried out on paraffin embedded sections. Isolectin $B_4$ from *Bandeiraea Simplicifolia* (BSI-$B_4$) predominantly binds α-D-galactose residues and has been identified as a selective marker for both resting and activated rat microglial cells (Streit and Kreutzberg, 1987). Dewaxed, rehydrated sections were pre-treated in the microwave for antigen retrieval (see below) and after washing in TBS, an endogenous peroxidase quenching step was carried out in 0.9% hydrogen peroxide in TBS. Sections were then washed in TBS and incubated with 20% normal horse serum in TBS for 45 minutes at room temperature in order to block non-specific protein binding sites. Sections were incubated overnight at 4° C. in a moist chamber with 35 μg/ml peroxidase-conjugated BS-I-$B_4$ (Sigma Chemical Co., USA) diluted in TBS. Sections were washed in TBS and colour-developed with nickel intensified DAB.

2. Microwave Pretreatment

Dewaxed, rehydrated sections, were placed in racks in a plastic tub containing 0.01M citrate buffer, pH 6.0 and placed in a 750 W microwave (PolarPatent, Euroserv, UK) with a tub of distilled water, to act as a heat sink. Aeration tubes were placed in the citrate buffer and bubbled gently to ensure an even distribution of temperature. A temperature probe was also placed in the citrate buffer.

The microwave was run on continuous power at 100% until the citrate buffer had begun to boil. At this point the power was reduced to 50% and the sections were allowed to cool to RT in the citrate buffer (approximately 20–30 minutes). Sections were rinsed in two changes of TBS, prior to commencing with the ICC or lectin staining protocol.

3. 22C11 Immunochemistry for APP in Paraffin Sections

Sections were dewaxed and rehydrated. Antigen retrieval was carried out in the microwave as described above. The sections were then washed three times in TBS for 5 minutes each time, before being soaked in 0.1% Triton X-100 in TBS for 30 minutes at room temperature, then in 0.9% $H_2O_2$/TBS for 30 minutes. A further TBS wash was then performed three times, for 5 minutes. Blocking was performed in 20% normal horse serum/TBS for 45 minutes at room temperature.

Incubation with antibody 22C11 (Boehringer Mannheim) diluted 1:200 in TBS was performed overnight at 4° C. The sections were washed three times in TBS to remove non-bound antibody. Secondary antibody (biotinylated anti-mouse IgG from Vector was then added diluted at 1:100 in TBS for 30 minutes at room temperature. After a further TBS wash, Vectastain Elite ABC kit (Vector, UK) was added in accordance with the manufacturer's instructions for 30 minutes at room temperature.

The colour was developed in 300 ml Sodium Acetate buffer pH6 (8 g Sodium Acetate in 1L d$H_2$O, 0.25 ml Glacial Acetic Acid), 75 mg DAB, 7.5 g Nickel Sulphate, 200 μl 30% $H_2O_2$, for 5 minutes at room temperature. The sections were then washed in tap water for 10 minutes at room temperature. The sections were then dehydrated as described above and mounted in DPX.

4. Ox-6 Immunochemistry for Rat Ia Antigen (MHC class II) in Paraffin Sections.

Antigen retrieval was carried out by incubation in 0.1% trypsin (from porcine pancreas, τ-irradiated, Sigma USA) in TBS, for 20 minutes at room temperature followed by extensive rinsing in TBS. The rest of the procedure was performed exactly as for 22C11 but with OX-6 monoclonal antibody (Serotec, UK) diluted at 1:200 in TBS.

5. Results

Statolon-infused animals demonstrated APP immunoreactive deposits in the following areas—Nucleus Acumbens, Striatum, Septum, and occasionally the cingulate cortex demonstrated areas of deposits that were sparse to moderate in density. The molecular layer of the dentate gyrus showed moderate to dense deposition. The CAI region of the hippocampus in the stratum oriens and radiatum, the anterior nucleus of the thalamus, the lateral geniculate body and the lateral nucleus of the thalamus posterior part showed extremely dense deposition of APP immunoreactivity. No APP immunoreactive deposits were observed in control animals. These animals also demonstrated a widespread activation of microglial cells, in terms of an increase in density and increased lectin binding in comparison to controls, which was present throughout the brain. The increase in density of microglial cells was extremely marked in the areas where APP immunoreactive deposits were observed. Microglial reactivity in areas of dense deposition was accompanied by MHC class II expression. Microglia also took on a more bushy appearance with slightly retracted processes that were more densely arborised.

Treatment With Anti-inflammatory Drugs

1. Protocol

Treatment with Ibuprofen was commenced one week prior to implantation of the mini-osmotic pump and continued for the duration of survival (28 days). Ibuprofen was administered in the drinking water, with the aim of delivering 0.01 of the LD 50, 2.63 mg/rat/day. This was achieved with a solution of 0.175 mg/ml on the assumption that rats would consume approximately 15 ml water/day.

2. Results

Of the Statolon-infused rats that were treated with Ibuprofen, only one showed a similar deposition distribution to those treated with Statolon only. The other two animals had only a very sparse distribution of APP immunoreactive deposits in the hippocampal CAI region and dentate gyrus. One had a reasonably dense deposition in the anterior thalamus but neither had any APP immunoreactivity in the posterior part of the lateral thalamic nucleus or the lateral geniculate body. Microglial density and lectin binding was also increased throughout the brain and particularly in the above-mentioned areas compared to controls. However, the density of microglia did not reach anything like that observed in the areas of deposition in the rats treated with only Statolon. MHC class II expression was similarly reduced.

What is claimed is:

1. A method of producing a non-human mammalian model of chronic cerebral inflammation comprising the step of introducing a double stranded RNA polynucleotide directly into the brain of a non-human mammal wherein the double stranded RNA polynucleotide does not encode amyloid precursor protein and wherein the double stranded RNA produces a chronic cerebral inflammatory response in said mammal.

2. The method of claim 1 wherein the double-stranded RNA polynucleotide is composed of single stranded RNA that is exogenous to the mammal.

3. The method of claim 1 wherein the double-stranded RNA polynucleotide is composed of recombinantly produced single-stranded RNA.

4. The method of claim 1 wherein the double-stranded RNA polynucleotide is a synthetic polynucleotide.

5. The method of claim 1 in which the mammal is a rodent.

6. The method of claim 5 in which the mammal is a rat.

7. The method of claim 1 in which the RNA polynucleotide is injected into the brain of the non-human mammal.

8. The method of claim 7 in which the RNA polynucleotide is injected into the cerebral ventricles of the brain of the non-human mammal.

9. The method of claim 1 in which the introduction of the RNA polynucleotide is performed with an osmotic minipump.

10. A non-human mammalian model for use in testing the effects of a chemical compound against chronic cerebral parenchymal inflammation wherein said model is produced by the method of claim 1 wherein the double stranded RNA produces a chronic cerebral inflammatory response in said mammal.

11. The method of claim of claim 1 wherein the exogenous polynucleotide is introduced into the brain of the mammal by a mini-osmotic pump, a needle, a syringe, or microdialysis.

12. The method of claim 1 wherein the RNA polynucleotide comprises polynucleotide analogues.

13. The method of claim 12 wherein the RNA polynucleotide comprise modified chemical groups.

14. The method of claim 1 wherein the RNA polynucleotide comprises statolon.

15. The method of claim 1 wherein the RNA polynucleotide is polyinosinic-poly-cytidilic acid.

16. A method of screening the potential therapeutic or prophylactic properties of a chemical compound against chronic cerebral inflammation comprising the steps of:

a) providing a non-human mammal;
   b) introducing directly into said non-human mammal's brain a double-stranded RNA polynucleotide that does not encode amyloid precursor protein;
   c) administering the chemical compound to the non-human mammal; and
   d) evaluating the response of the non-human mammal to administration of the chemical compound by observing the change in the chronic cerebral inflammation in said mammal wherein a decrease in the chronic inflammation indicates the chemical compound has potential therapeutic or prophylactic properties.

17. The method of claim 16 in which the step of administering the chemical compound is performed before the step of introducing the polynucleotide.

18. A method of screening the potential therapeutic or prophylactic properties of a chemical compound against chronic cerebral inflammation comprising the steps of:

a) providing a non-human rodent;
   b) introducing directly into said rodent's brain a double-stranded RNA polynucleotide that does not encode amyloid precursor protein;
   c) administering the chemical compound to the rodent; and
   d) evaluating the response of the rodent to administration of the chemical compound by observing the change in the chronic cerebral inflammation in said mammal wherein a decrease in the chronic inflammation indicates the chemical compound has potential therapeutic or prophylactic properties.

19. A method of producing a non-human mammalian model of chronic cerebral inflammation comprising the steps of providing a non-human mammal and introducing an exogenous double-stranded RNA polynucleotide directly into the brain by injection, mini-osmotic pump, needle or microdialysis of said non-human mammal wherein the polynucleotide generates a chronic cerebral inflammatory response in said mammal and wherein the RNA polynucleotide does not encode amyloid precursor protein.

* * * * *